United States Patent [19]

Hammerslag et al.

[11] Patent Number: 5,287,858
[45] Date of Patent: Feb. 22, 1994

[54] ROTATIONAL ATHERECTOMY GUIDEWIRE

[75] Inventors: Julius G. Hammerslag, San Juan Capistrano; Vincent Divino, Mission Viejo, both of Calif.

[73] Assignee: Pilot Cardiovascular Systems, Inc., San Clemente, Calif.

[21] Appl. No.: 949,908

[22] Filed: Sep. 23, 1992

[51] Int. Cl.⁵ .............................................. A61B 5/02
[52] U.S. Cl. ............................ 128/772; 606/170; 606/180
[58] Field of Search ................ 128/657, 772; 604/22; 606/167, 170, 180

[56] References Cited

U.S. PATENT DOCUMENTS

| | | |
|---|---|---|
| 3,789,841 | 2/1974 | Antoshkiw . |
| 4,445,509 | 5/1984 | Auth ............................ 604/266 |
| 4,538,622 | 9/1985 | Samson et al. ................ 128/772 |
| 4,545,390 | 10/1985 | Leary . |
| 4,561,807 | 12/1985 | Hilse et al. .................... 406/99 |
| 4,591,355 | 5/1986 | Hilse ............................. 604/159 |
| 4,616,653 | 10/1986 | Samson et al. ................ 604/95 |
| 4,646,736 | 3/1987 | Auth . |
| 4,679,557 | 7/1987 | Opie et al. .................... 128/752 |
| 4,763,647 | 8/1988 | Gambale ....................... 128/772 |
| 4,858,810 | 8/1989 | Intlekofer et al. ............. 226/127 |
| 4,867,173 | 9/1989 | Leoni ............................ 128/772 |
| 4,884,579 | 12/1989 | Engelson ....................... 128/772 |
| 4,923,462 | 5/1990 | Stevens ......................... 606/159 |
| 4,940,062 | 7/1990 | Hampton et al. .............. 128/772 |
| 4,955,384 | 9/1990 | Taylor et al. .................. 128/657 |
| 4,962,755 | 10/1990 | King et al. .................... 604/22 |
| 4,971,490 | 11/1990 | Hawkins ........................ 128/772 |
| 4,990,134 | 2/1991 | Auth ............................. 604/22 |
| 5,026,384 | 6/1991 | Farr et al. ..................... 606/180 |
| 5,112,345 | 5/1992 | Farr .............................. 606/180 |
| 5,144,959 | 9/1992 | Gambale et al. ............... 128/772 |

OTHER PUBLICATIONS

Heart Technology, Inc. Brochure, *Put Our Diamonds in the Rough*, Introducing Rotablator, Jun. 1991.
*Design News*, Sep. 23, 1991.

*Primary Examiner*—Max Hindenburg
*Attorney, Agent, or Firm*—Knobbe, Martens, Olson & Bear

[57] ABSTRACT

Disclosed is a guidewire particularly suited for use in rotational atherectomy. The guidewire has increased lateral flexibility in the distal region, and a substantially constant diameter throughout. The exterior diameter at any point is substantially equal to the sum of the diameter of the central core wire, and twice the diameter of the wire of the spring coil, if any, mounted thereon. At proximal portions of the guidewire, the outer spring coil may be deleted.

10 Claims, 5 Drawing Sheets

ROTATIONAL ATHERECTOMY GUIDEWIRE

BACKGROUND OF THE INVENTION

The present invention relates generally to guidewires for catheters and the like, and more particularly to a guidewire for use in a rotational atherectomy procedure.

Medical catheters generally comprise elongate tube-like members which may be inserted into the body, either percutaneously or via a body orifice, for any of a wide variety of diagnostic or therapeutic purposes. Such medical applications frequently require use of a catheter having the ability to negotiate twists and turns, particularly with regard to certain cardiovascular applications.

One such application, rotational atherectomy, requires manipulation of a catheter from a position outside the patient's body through extended portions of the patient's arterial system to position a cutting tip at a stenotic site. Stenosis is an abnormal narrowing of a passage or canal in the body, commonly associated with atherosclerosis, or blocking of the arteries with plaque.

Rotational atherectomy utilizes a rapidly rotating cutting tool at the distal end of the catheter for transluminal recanalization of intravascular lesions of soft or hard thrombotic or atheromatous material. The procedure is more formally known as Percutaneous Transluminal Rotation Ablation (PTRA).

One commonly used rotational atherectomy device is made by Heart Technology, Inc. and marketed under the name "Rotablator ®". The Rotablator consists generally of an advancer/catheter, a guidewire, a console and a power source of air or nitrogen. Thousands of microscopic-sized diamond crystals coat the forward face of an elliptical-shaped polishing tip. With each revolution, these crystals remove tiny scoops of plaque from the artery. The cutting tip comes in a variety of sizes ranging from 1.25 mm to 4.5 mm.

The particles, much smaller than a red blood cell, are said not to present a threat of injury by lodging in the patient's cardiovascular system. During a plaque removal procedure, only a few thousandths of a pound of the tiny plaque particles are released into the bloodstream. The body's reticuloendothelial system is believed to naturally remove as much as a pound of impurities from the blood supply each month.

The diamond cutting surfaces are said to easily remove even the hardest calcified plaque. The Rotablator is said to be useful for virtually all lesion types, including long, calcified, eccentric, and distal. The patient is left with a smooth, patent lumen. Success in the rotational atherectomy procedure is defined as a lesion with less than 50% residual stenosis and a 20% absolute improvement in the luminal diameter.

In general, the catheter comprises a small diameter, triple-helix wound tubular shaft with a cutting tip on its distal end. An air turbine causes the tubular shaft and cutting tip to rotate around the guidewire and within an outer Teflon sheath at speeds of up to 200,000 rpm. The Rotablator catheter tracks over a constant 0.009-inch diameter solid guidewire. The rotational atherectomy procedure produces a smooth, polished luminal hole and is said to lessen the occurrences of elastic recoil, flaps, and vessel dissections, commonly associated with balloon dilatation.

In a typical rotational atherectomy procedure, the guidewire is transluminally inserted into the brachial or the femoral artery, and advanced to the stenotic region. The rotatable catheter is then mounted over the guidewire and advanced to the treatment site. Coronary arteries are tortuous, have many sub-branches, and often the obstruction is either located where the diameter of the artery is small or, by its very presence, the obstruction leaves only a very small opening through which a guidewire and/or catheter can be passed. Consequently, the cardiologist often finds it difficult to maneuver the guidewire or catheter, which are typically several feet long, from the proximal end. Often, the solid guidewire used in current rotational atherectomy procedures does not have sufficient flexibility at its tip to negotiate the complex system of arteries within the patient.

In contrast, guidewires currently used for percutaneous transluminal coronary balloon angioplasty applications taper from a relatively large proximal diameter down to as little as a 0.003-inch diameter near the distal end, thus permitting greater flexibility at the tip. However, using such a tapered guidewire is generally unsatisfactory in a rotational atherectomy procedure because there is insufficient strength at the thinned distal end of the guidewire to support the rotating burr. In addition, the loose spring coil segment which typically covers the tapered distal portion of the core wire in the known coronary angioplasty guidewires tends to "unwind" inside rotating atherectomy catheter.

Thus, there remains a need for a guidewire which is especially suited for procedures such as rotational atherectomy. In particular, the guidewire should preferably be constructed in a manner such that the tip is both more laterally pliable in bending than the current rotational atherectomy guidewires, and yet better able to support a rotating sleeve and cutting tip than prior tapered core wire angioplasty guidewires.

SUMMARY OF THE INVENTION

In accordance with one aspect of the present invention, there is provided a guidewire such as for use in a rotational atherectomy procedure. The guidewire comprises an elongate flexible core wire having a proximal segment with a first diameter and at least one distal segment having a second smaller diameter.

A first coil is disposed about the distal segment, and in contact or else in close proximity with the core wire throughout the length of the coil. Preferably, the outer diameter of the first coil is substantially the same as the outer diameter of the proximal segment of the core wire to provide a guidewire having a substantially uniform exterior profile throughout. Preferably, the outer diameter of the guidewire is approximately 0.009 inches.

In accordance with a further aspect of the present invention, there is provided a rotational atherectomy catheter system, comprising a source of rotational energy, and an elongate tubular catheter having a central lumen extending axially therethrough and rotationally linked to the source of rotational energy.

A guidewire is movably disposed within the central lumen. The guidewire comprises a core wire and a spring coil wrapped about at least a portion of the length of the core wire, said coil wrapped about the core wire in the same rotational direction as the direction of rotation of the tubular catheter during operation. Preferably, the coil is wrapped snugly against the core wire, throughout the length of the coil.

In accordance with a further aspect of the present invention, there is provided a rotational atherectomy method. In accordance with the method, a guidewire is inserted into a body lumen and advanced to the treatment site. The guidewire comprises a solid core having at least one transition thereon between a proximal segment having a first diameter and a distal segment having a second diameter. A coil is snugly wrapped around the distal portion of the core wire, and comprises a coil wire having a diameter such that the exterior diameter of the coil is substantially the same as the exterior diameter of the proximal segment of the core wire.

A rotational atherectomy catheter is thereafter advanced distally over the guidewire, and the catheter is thereafter rotated in the same rotational direction as the loops of the coil, so as to prevent unwinding of the coil under the rotational force of the rotational atherectomy catheter.

These and further features and advantages of the present invention will become apparent from the detailed description of preferred embodiments which follows when considered together with the attached drawings and claims.

BRIEF DESCRIPTION OF THE INVENTION

DETAILED DESCRIPTION OF THE INVENTION

Figures 1, 1A:
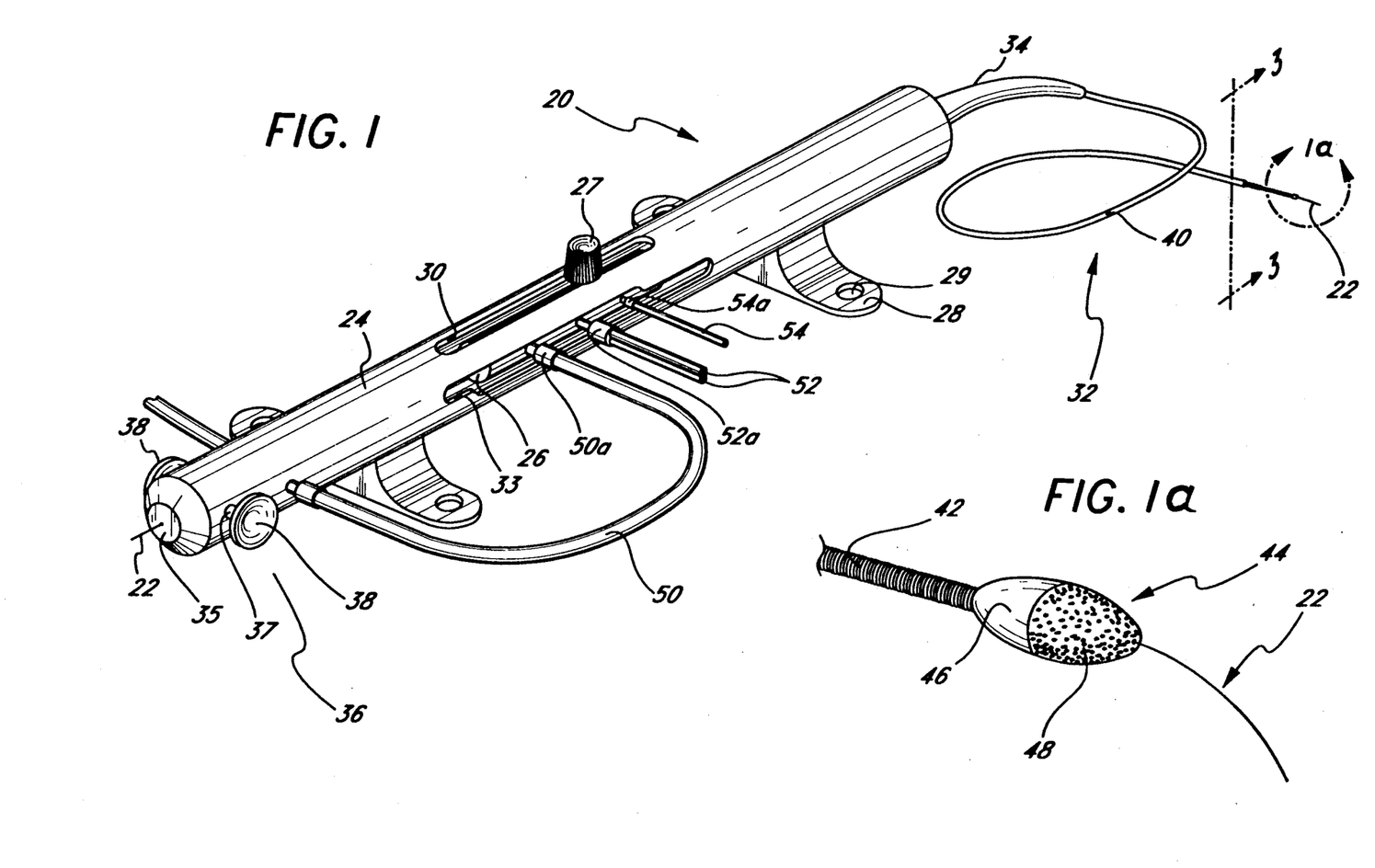
FIG. 1 is a schematic view illustrating the components of a typical rotational atherectomy system including the improved guidewire of the present invention.
FIG. 1a is a detail of the distal end of the catheter of the system of FIG. 1 with the guidewire extending through the ablating burr.

Referring to FIG. 1, there is shown a rotational atherectomy device 20 including an improved guidewire 22 of the present invention. The guidewire 22 is particularly suited for use in the device 20, however, the description of the present invention in the context of a rotational atherectomy procedure is not meant to be limiting. Similar surgical or other procedures benefitting from a guidewire with the properties described herein are within the range of applications of the present guidewire 22.

The rotational atherectomy device 20 generally comprises a tubular body 24, having an internal drive motor (not illustrated) within an axially slidable housing 26. A handle 27 is connected to the housing 26 to advance and retract the rotating tip as will be discussed. A shaft (not illustrated) of the handle 27 extends through an upper elongated slot 30 to link the handle 27 to the slidable housing 26. An elongated catheter body 32 extends from a flexible sleeve 34 at the distal end of the body 24. A pair of lower outwardly extending feet 28 with mounting holes 29 provide means to attach the tubular body 24 to an operating support table.

A console (not shown) controls and monitors the drive motor via air hose 50 which is attached to the internal slidable housing 26 through an elongated slot 33 on the side of the tubular body 24. The slot 33 on the side of the tubular body 24 is slightly longer than the upper elongated slot 30 for the handle 27 to accommodate the full travel of the handle 27 without impacting the air hose 50 or conduit 54 with the tubular body. The proximal portion of the guidewire 22 is shown extending out the rear face 35 of the tubular body 24, and the guidewire extends in an unobstructed path through the tubular body and the entire length of the catheter 32.

Figure 2:
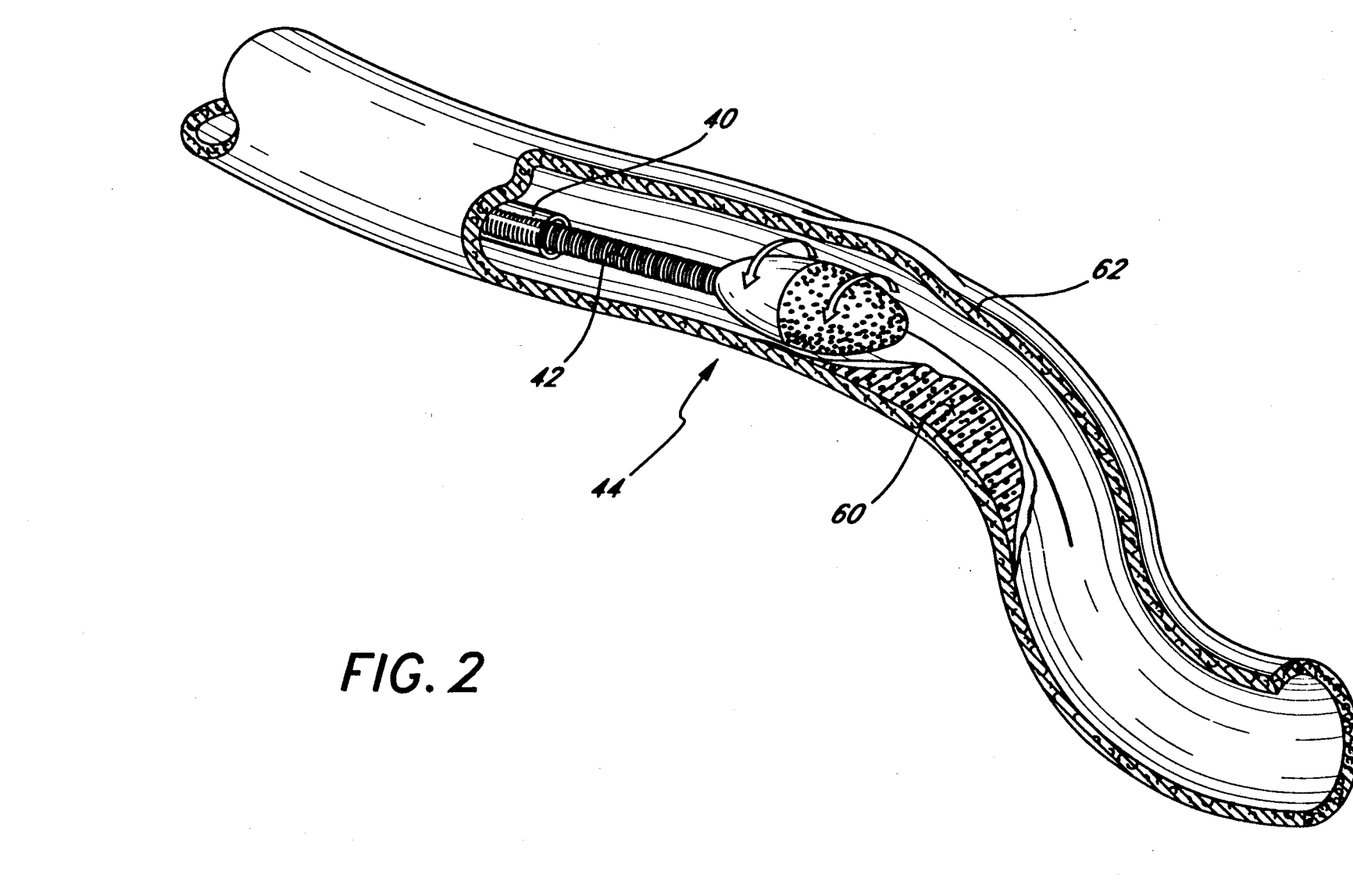
FIG. 2 is a partial cutaway view of a blood vessel showing a rotational atherectomy being performed in conjunction with the improved guidewire of the present invention.

As seen in FIGS. 1 and 2, the catheter body 32 further comprises an outer sheath 40, a rotatable hollow tubular sleeve 42 sized to rotate within the sheath 40. The guidewire 22 is removably disposed within a central lumen of the rotatable sleeve 42. The rotatable sleeve 42 may be a solid-walled tube, or, preferably, a coil such as a triple-helix wound matrix of wires defining the central lumen.

Referring to FIG. 1a, a cutting burr 44 typically comprises a rotatable support structure 46 coated with fine diamond crystals 48 or other cutting surface. Burr 44 is affixed at the distal end of the rotatable sleeve 42. In a typical procedure, the rotatable sleeve 42 turns the cutting burr 44 at speeds of up to 200,000 rpm. The cutting burr 44 works on the principle of differential cutting—a process by which the tiny diamond crystals 48 preferentially ablate the inelastic plaque while the healthy elastic arterial wall deflects away unharmed.

The drive motor inside tubular body 24 is coupled to the rotatable sleeve 42 in order to impart rotation thereto. The motor may be powered by any of a variety of known means; however, an air-driven turbine is preferred for its high-speed, low-vibration and low-inertia characteristics. Thus, in a preferred embodiment, an air hose 50 attaches to the slidable housing 26 within tubular body 24 such as through a fitting 50a. The air hose 50 provides pneumatic power to the air driven turbine. A pair of fiber optic conduits 52 also attach to the side of the slidable housing 26 through a fitting 52a to monitor the speed of the turbine. The rotational speed information is processed and displayed at the console.

A sterile fluid connection 54a is also provided in the side of the slidable housing 26 to attach an IV conduit 54 through which saline solution or other fluid may be supplied, the flow rate being controlled either through the console or through other means known in the art. The saline solution is applied to the cutting site such as by flowing within the stationary outer sheath 40 to both lubricate the rotating burr 44 and reduce the heat generation at the operating site, and also to reduce friction between the rotating catheter sleeve 42 and outer sheath 40.

A brake assembly 36 allows the surgeon to easily halt the rotation of the motor and rotatable sleeve 42 on demand. The brake assembly 36 is controlled with a shaft 37 having opposing thumb and forefinger members 38 near the rear end 35 of the tubular body 24 which, by depressing one or the other, alternately apply and release the brake. Typically, a braking mechanism would include some means for shutting off the flow of air through the air hose 50 by pinching the flexible hose. Upon application of the brake 36, the rotating burr 44 and sleeve 42 stop relatively quickly as the air-driven turbine has a very low inertia. However, the same low inertia enables the air turbine to be brought up to operating speed very rapidly when the brake 36 is released.

A suitable rotational atherectomy system for use with the guidewire 22 of the present invention can be obtained from Heart Technology, Bellevue, Washington, under the trade name Rotablator ®.

The rotational atherectomy procedure for ablating a plaque deposit within an artery is generally accomplished as follows. The distal tip of the guidewire 22 is typically first prebent and then inserted into a small incision in the femoral or brachial artery, and advanced to the stenotic region. The surgeon manipulates the guidewire 22 through often tortuous, convoluted arterial passageways to the obstruction by torquing or otherwise steering the guidewire 22. A radio opaque marker or other indicator is used to assist the surgeon in locating the distal tip of the guidewire 22 and positioning it at the stenotic region.

After the guidewire 22 is in position, the catheter 32 is advanced over the proximal end of the guidewire 22 and distally into the patient, with the wire 22 extending through the lumen of rotatable sleeve 42. The catheter 32 is advanced distally until the burr 44 is positioned near the treatment site.

As illustrated in FIG. 2, the removal of plaque 60 is accomplished by rotating the sleeve 42 to cause the burr 44 to scrape against the narrowed walls of the deposit. The handle 27 connected to the internal slidable housing 26 allows the surgeon to longitudinally advance or retract the rotating sleeve 42 and burr 44 within the outer sheath 40 and over the guidewire 22. The surgeon is thus able to nudge the rotating burr 44 slowly across the plaque deposit 60 while experiencing a certain tactile feedback through the handle 27. The longitudinal distance traveled is limited by the length of the elongated slots in the tubular body 24, which may be made shorter or longer depending on the anticipated size of deposit 60. Clinical statistics have shown that approximately 50% of lesions are less than 5 cm long.

The stationary outer sheath 40 extends distally to a point just proximal of the operating burr 44, and protects the vascular intima 62 from injury while allowing the sleeve 42 to rotate with minimal friction within. The ablation procedure is generally relatively short, once the guidewire is in place, such as within the range of from about 1 minute to about 15 minutes, rendering the time spent in location and placement of the guidewire 22 a significant portion of the procedure time.

Figure 3:
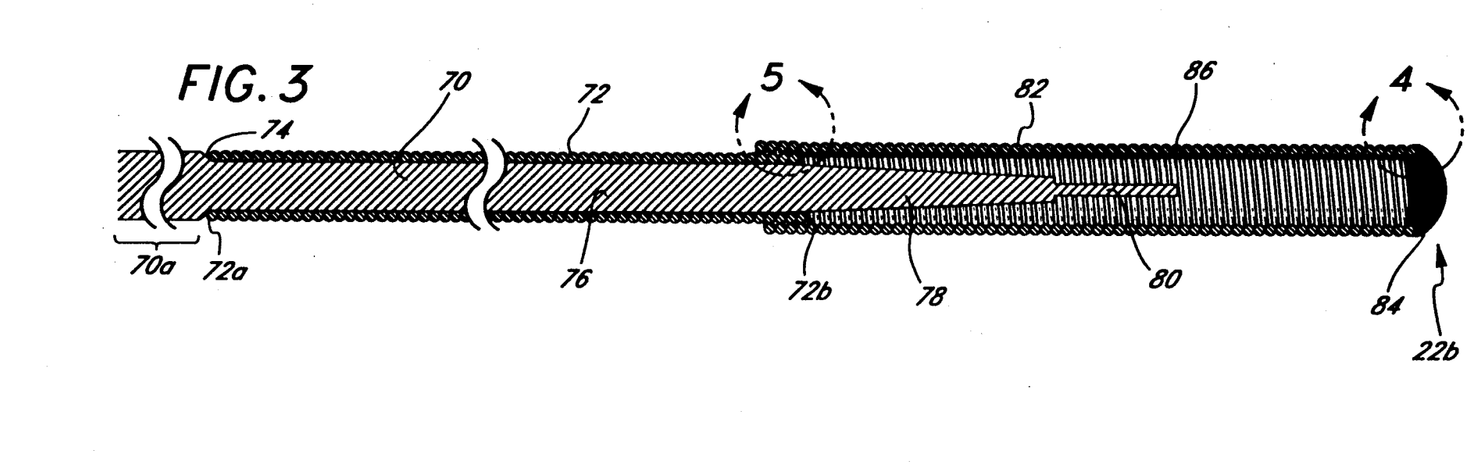
FIG. 3 is a cross-sectional view of the distal end of the guidewire of the present invention taken along line 3—3 of FIG. 1.

Referring to FIG. 3, the preferred guidewire 22, in accordance with the present invention, generally comprises an elongate core wire 70 having a spring coil 72 wound around at least a distal portion thereof. The core wire 70 is preferably a solid wire having a proximal section 70a of its length with an outside diameter suitable for passage through the guidewire lumen of catheter 32, rotating sleeve 42, and cutting burr 44. In general, the diameter of proximal portion 70a will be no more than about 0.012 inches, and preferably is no more than about 0.009 inches although other sizes can be readily envisioned depending upon the intended application.

A transition taper 74 separates a reduced diameter portion 76 from the proximal section 70a. The view of FIG. 3 is out of scale to facilitate illustration. In one embodiment, the length of the proximal portion 70a of the wire 22 is approximately 2.7 m, and the length of the distal portion (from the transition taper 74 to the tip 22b) is approximately 30 cm.

At least one section of outer spring coil 72 is wrapped around the reduced diameter portion 76. The coil 72 may be tightly wrapped around the portion 76, or prewound and slidingly fitted over the portion, depending on the particular manufacturing method, as will be described below. Coil 72 extends distally from the transition taper 74. The coil 72 is sized such that when wrapped around reduced portion 76, the outer diameter of the coil 72 is substantially the same as the outer diameter of the proximal solid portion 70a of the core wire to produce a guidewire having a substantially uniform diameter throughout. The coil 72 is preferably in contact with the reduced core wire section 76 throughout the length of the coil 72, and preferably, the coil is snugly fitted against the core. Alternatively, the coil 72 is slidingly fitted over the reduced section 76 with a slight clearance and thus is in contact due to the force of gravity.

The coil 72 is rotationally fixed with respect to the core wire 70 such as by securing the proximal end 72a of the coil to the transition taper 74 with solder or other means known in the art. Likewise, the distal end 72b of the coil is preferably attached to the core wire 76 with solder, brazing or other means known in the art. Alternatively, the coil 72 can be secured throughout its length to the core wire 76, or at specific "spot welds" periodically along its length. Preferably, however, the coil 72 is attached to the core wire 76 only at the ends of the coil, since this advantageously optimizes the lateral flexibility of the distal region of the guidewire 22.

The spring wrapped reduced diameter portion 76 of core wire 70, in accordance with the present invention, results in a more laterally flexible region at the distal end of the guidewire 22 when compared to currently used solid core wires of constant equivalent diameter throughout. The improved flexibility of the distal region facilitates the navigation of the guidewire 22 through the arterial network, much like the tapered core wire guidewires for balloon angioplasty procedures. Unlike conventional PCTA guidewires, however, the present invention provides sufficient support for a rotational atherectomy catheter, and does not tend to unwind while carrying an outer rotating sleeve.

The present inventors have determined that winding the coil 72 around at least a distal segment of central core wire 70 can provide an assembled guidewire 22 having a substantially constant diameter throughout, yet adds only minor lateral stiffness to the tapered core at this region. The coil 72 does, however, add significantly to the ability of the guidewire to support the rotating burr 44. This is due to the substantially continuous cross-sectional area of material the coil 72 provides when it is torqued and tightens against the core wire 70. The coil 72 may have some clearance with the core wire 70. This configuration results in only a minimal reduction in torsional strength at the section with the coil wire 72. Upon rotation of the rotatable sleeve 42, the flexible region resists knotting or kinking from frictional forces generated between the two members, and substantially eliminates the possibility of torsional failure.

Extending distally from the reduced portion 76 of the core wire, at least one additional diameter reduction such as taper 78 narrows radially inwardly in the distal direction. The first coil 72 is preferably soldered to the core wire at about the proximal end of elongated taper 78. The taper 78 preferably terminates in a generally constant diameter portion 80 at the very distal tip of the core wire. This constant diameter tip 80 is optimally flattened between rollers during manufacturing to form a ribbon.

In the embodiment illustrated in FIG. 3, a second coil 82 extends from about the distal end 72b of the first coil 72 to the distal tip 22b of the guidewire 22. Preferably, the second coil 82 overlaps the first coil wire 72 to facilitate attachments as will be discussed. The inside diameter of coil 82 is approximately equal to the outer diameter of the first coil 72. The second coil 82 terminates at the distal tip 22b where it is preferably provided with a hemispherical solid plug 84, generally consisting of solder. The second coil wire 82 thus encloses the distal tip 80 of the core wire 70. The second coil 82 permits an added amount of lateral flexibility at the extreme distal end of the guidewire.

As seen FIG. 3, a safety ribbon 86 preferably extends from the distal portion of the first coil 72 to the distal tip 22b of the guidewire. The safety ribbon 86 is affixed at both its proximal and distal ends as is known in the art. The safety ribbon 86 thus provides a means for retracting the distal tip 22b of the guidewire in case of a break in second coil 82.

Suitable core wire may be prepared in any of a variety of manners which can be readily devised by one of skill in the art. In one embodiment, a spring hardness solid stainless steel wire of 0.009 inch diameter and 300 cm length is obtained from sources known to those of skill in the art. The core stock is thereafter preferably straightened such as by Starguide of Denver, Colorado.

The straightened wire is thereafter ground to the desired profile such as by Microguide, Tahachepi, California. Preferably, the reduced portion 76 is ground to a diameter of about 0.0054 inches, so that when wrapped with 0.0017 inch coil wire, the assembled diameter through the coil 72 will be slightly less than 0.009 inches.

The transition 74 is thereafter inspected for structural integrity. The transition 74 typically has an axial length of about 2.5 mm and separates the milled 0.0054 inch reduced outside diameter portion 76 of the core wire. The elongated taper 78 begins approximately 12 mm from the distal tip of the core wire. The elongated taper 78 extends about 8 mm in the distal direction from the 0.0054 inch milled portion 76 to a 0.0025 inch diameter tip 80. The constant diameter tip 80 of the core wire has a length of about 4 mm, and is flattened between rollers to a dimension of approximately 0.001 by 0.005 inches. Of course, alternative techniques and design specifics can be readily envisioned by those of skill in the art, which also embody the present invention.

The coil 72 is thereafter wound or mounted around the reduced central core 76 such that the loops of the coil extend in the direction of rotation of sleeve 42 to prevent an unwinding action. Winding the coil 72 in this direction further strengthens the guidewire 22 torsionally as the rotating sleeve 42 tends to tighten the coil around the central core 76.

The coil 72 may be constructed in any of a variety of ways known in the art, such as by tightly winding a coil of wire directly around the central core 76, or by separately winding the coil and mounting the coil onto the core wire as a separate step. In the latter method, the coil 72 is preferably wound around a rotating mandrel having a diameter equal to or slightly smaller than the diameter of milled segment 76, to ensure a snug fit in the assembled wire.

Preferably, 0.0017 inch diameter wire stack is wound into a coil over a 0.005 inch diameter mandrel. The coil springs open slightly upon release from the mandrel to approximately a 0.0054 inch inside diameter. The coil 72 is thereafter slid onto the core wire 70, and soldered at the transition taper 74 and at the proximal end of the elongated taper 78. At least the solder joint 88 at the proximal end of the elongated taper 78 is a high temperature solder, for reasons that will follow.

Figure 4:
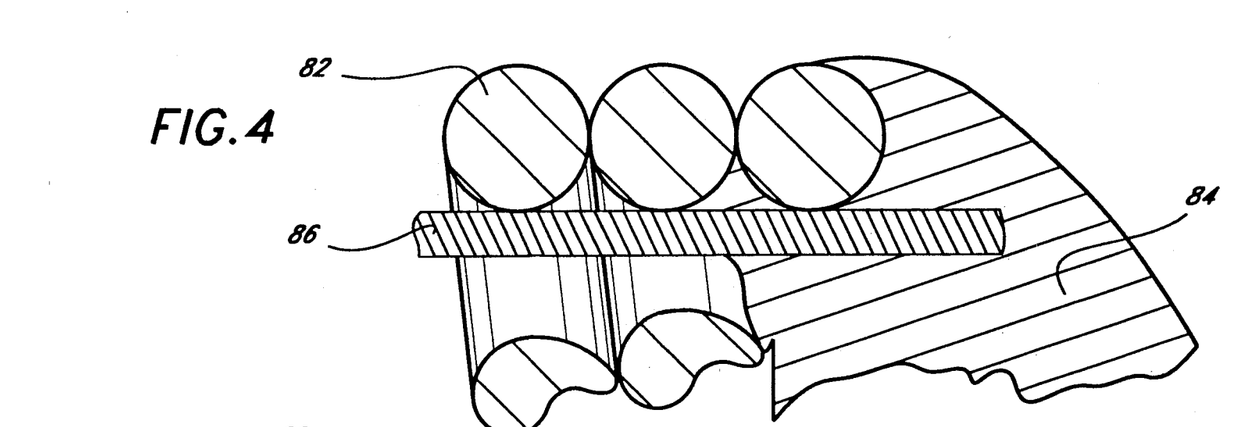
FIG. 4 is a detail of the terminal end of the guidewire of FIG. 3.
Figure 5:
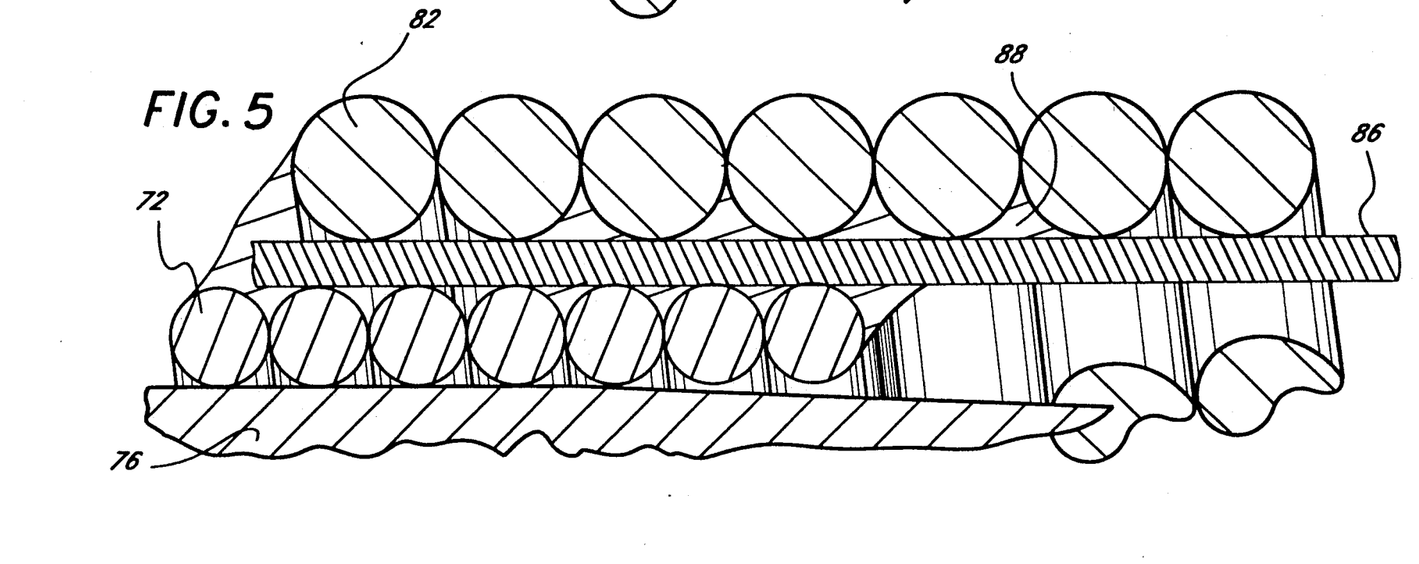
FIG. 5 is a detail of a distal portion of the guidewire of FIG. 3 illustrating the attachment of the safety ribbon.

A 0.001 inch by 0.003 inch safety ribbon 86 is held in position as illustrated in FIG. 3 and in more detail in FIGS. 4 and 5. The second coil 82, which in this embodiment has a length of about 20 mm and an outside diameter of about 0.014 inches, is advanced proximally over the distal end of the core wire 70 to trap the proximal end of ribbon 86 as illustrated. The safety ribbon 86 and second coil 82 are soldered 90 to the first coil at the proximal end of the elongated taper 78, using a relatively low temperature solder. This is so that the step of soldering the outer coil 82 and the safety ribbon 86 into place does not reliquify the solder joint 88 which already exists at about that point. The safety ribbon 86 extends in between the two coils, and into the solder joint. The distal opening of the second coil, with the safety ribbon 86 extending therethrough, is closed by the solder plug 84 which forms the tip 22b of the guidewire. Any excess ribbon 86 is cut off at this point and also at the first solder joint.

The reduced milled portion 76 of the core wire preferably has a diameter within the range of from about 0.0052 to about 0.0056 inches. Sections having a diameter as low as about 0.0045 inches will probably also exhibit the beneficial features of the present invention, when combined with an appropriately sized outer coil in order to make the outside diameter of the coil equivalent to the proximal solid portion 70a of the guidewire 22. The maximum diameter of the reduced segment 76 of the core wire is limited by the minimum diameter acceptable for the adjacent coil 72. This minimum diameter is, for example, limited by the strength requirements of the coil 72.

Since the inside diameter of the coil 72 can be either increased or decreased by rotating one end of the coil with respect to the other end, the precise relationship between the native ID of the coil 72 and the core wire 70 is strongly influenced by manufacturing preferences. Preferably, the coil 72 has a sufficient native ID that it can be slidably mounted onto the core wire 70 with relative ease. One end is then affixed to the core wire 70 and the second end may be rotated if necessary to bring the body of the coil in snug contact with the core wire before affixing the second end. This snug fit is preferred, however some minimal clearance between the coil 72 and core wire 70 is permitted, such clearance, however, may not exceed the thickness of the core wire.

The coil 72 preferably comprises a high tensile strength wire of a resilient, non-corrosive metal such as stainless steel, titanium or platinum, and may have a circular cross section with a diameter of from about 0.001 to 0.003 inches. The wire may alternatively have a rectangular cross section of from about 0.001 to 0.003 inches by from about 0.001 to 0.004 inches, or other variations known in the art. Preferably, the diameter of the coil stock is selected such that the assembled guidewire has a substantially uniform external diameter throughout.

The exterior surface of the wound coil-type guidewire shaft is preferably smooth throughout, and optionally provided with an elastic, biocompatible coating or sheath to enhance the smooth outer surface. Suitable coatings can be formed by dipping, spraying or wrapping, and heat curing operations, as are known in the art. Alternatively, heat shrinkable tubing may provide a suitable outer sheath in some applications. A coating material should be selected which will permit sufficient flexing of the wire without cracking, will minimize sliding friction of the implement during insertion and removal, and is substantially chemically inert in the in vivo vascular environment. A variety of suitable materials are known, including, for example, polytetrafluoroethylene, urethane or polyethylene.

Bench tests of a 0.009 inch diameter guidewire in accordance with the present invention have shown its distal end to be approximately five times more flexible than the conventional solid 0.009-inch diameter rotational atherectomy wire. Tests have also shown that the torque capacity of the distal end of the improved wire of the present invention is approximately four times greater than the conventional guidewire in tortuous passages. Thus, the guidewire shown is both more flexible in bending, yet with better torque characteristics than the conventional solid uniform diameter guidewire conventionally used in rotational atherectomy procedures.

Figure 6:
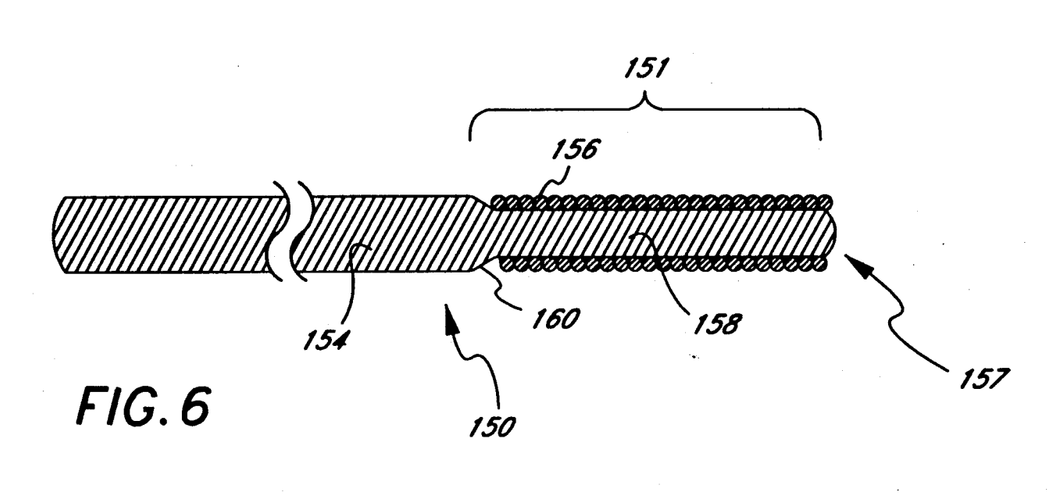
FIG. 6 is a simplified cross-sectional view of an alternative embodiment of the guidewire.

An alternative embodiment of guidewire is shown in simplified form in FIG. 6. Each of the embodiments shown in FIGS. 6 and 7 preferably are also provided with an entry coil, such as coil 82 in FIG. 3, to facilitate negotiation of branched passageways. The entry coil (not illustrated) preferably has dimensions on the order of 0.014 inches diameter by 2 cm length, although other dimensions can readily also be used, depending upon the intended application.

The embodiment of FIG. 6 generally comprises an elongate core wire 154 having a spring coil 156 wound around at least a distal portion thereof. The core wire is preferably a solid wire having at least one distal segment with a reduced diameter. In the illustrated embodiment, proximal solid shaft portion 158 is separated from a relatively reduced diameter distal region 151 by a tapered transition portion 160.

The coil 156 is wrapped around the central core 154 at the distal segment 151. The coil 156 is preferably in partial contact or else in close proximity with the core wire throughout the length of the coil, and more preferably, the coil is snugly fitted against the core along the length of the coil.

Referring to FIG. 6, one specific embodiment of the present invention comprises a guidewire 22 having a proximal segment 58 with a length of about 150 cm and a diameter of approximately 0.009 inch. A distal 30 cm section of the core wire has a diameter of about 0.006 inch and a taper is provided between the two sections. The tapered transition occurs over an axial length of about 2.5 mm. Although the length of the taper does not appear to be critical, the risk of fracture appears to increase as the taper approaches a right angle shoulder transition. In addition, an excessively long taper may result in an undesirably inflexible distal tip of the guidewire, depending upon the intended application.

Coil 156, soldered at both ends to the core, comprised 0.0015-inch diameter round stainless steel wire having a tensile strength of 444K psi, obtained from Fort Wayne Metals and identified as type 3040. The wire was wound about a 0.0055-inch mandrel. The external diameter of the finished wire was approximately 0.009 inch throughout.

Figure 7:
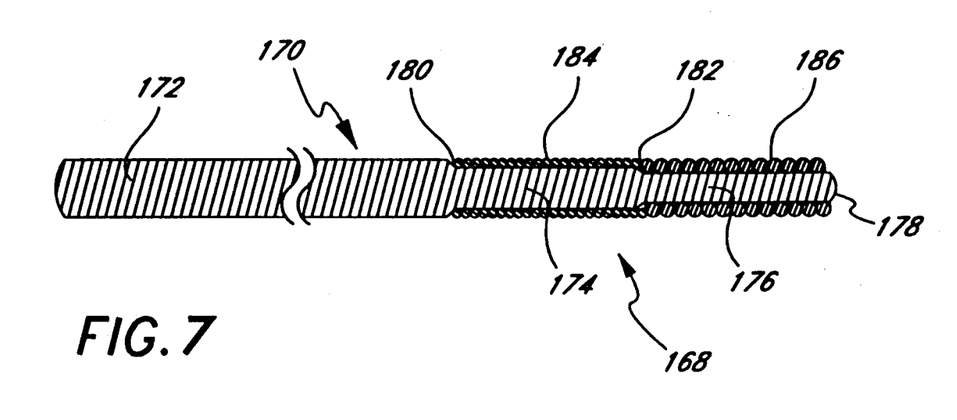
FIG. 7 is a simplified cross-sectional view of a second alternative embodiment of the guidewire.

Referring to FIG. 7, an alternative guidewire 168 comprises a solid core wire 170 having a proximal portion 172, at least one intermediate portion 174 and a distal portion 176. The flexibility of the guidewire 168 increases from the proximal portion 172 to the intermediate portion 174, and further in the distal portion 176. The principles and construction of the guidewire 168 are similar to the embodiment described above resulting in an even more flexible tip. Thus, the proximal portion 172 transitions to a smaller diameter intermediate portion 174 which, in turn, transitions to an even smaller distal portion 176 terminating in a tip 178. Two tapered steps 180, 182 provide the reduction in diameter.

In this embodiment, two different coils made form different diameter wire stock are wound around the core wire 170 at portions 174 and 176 so that the outer diameter of the assembled guidewire 170 remains substantially constant throughout. A first coil 184 is attached to the first taper 180 with solder and extends distally to at least one second point of attachment at or near the second taper 182 or to a second coil 186. The second coil 186 extends from the second taper 182 to the tip 178 and is soldered thereto. A distal taper such as tapered portion 78 (FIG. 3) may also be provided although for simplicity it has not been illustrated in FIGS. 6 and 7.

The embodiment in FIG. 7 illustrates a guidewire 168 having a torsional strength which is relatively constant along its entire length yet having lateral flexibility which increases in steps to the distal tip 178. The increased flexibility of the guidewire 168 further facilitates negotiation of the most complex arterial networks.

Other configurations are contemplated which more continuously increase the flexibility of the guidewire 170. For instance, a third, fourth or more flexible segments may be provided in the core wire. Alternatively, the central core wire may taper smoothly from the proximal segment 172 to the tip 178 without steps in diameter, and a coil made from wire with a continuously increasing diameter mounted around the core to retain the outer diameter of the shaft. Alternatively, distal portion 176 can be wrapped with two layers of the same diameter wire which is used to wrap intermediate portion 174. In an embodiment having an exterior coating, minor diameter deviations such as at the transition point between coils wound from different wire stock can more easily be tolerated.

For most rotational atherectomy procedures, the guidewire, in accordance with the present invention, is provided with a substantially uniform exterior diameter throughout. Thus, any transitions between solid outer core wire surfaces and spring coils, or between adjacent sections of spring coil, are preferably provided with a smooth exterior surface. This can be accomplished, in an embodiment having all metal parts, by flowing solder into the transition, followed by an optional polishing or grinding step. Although the embodiments disclosed herein have been in terms of metal core wires and metal coil, non-metal materials such as polymers, may also be utilized to construct the guidewires of the present invention, provided the physical properties of the materials used are suitable under the intended use environment.

At any particular point along the length of the guidewire, the outside diameter is substantially equal to the outside diameter of the core wire at that point, plus twice the diameter of the wire from which the coil stock was manufactured. As has been discussed, the proximal portion of the guidewire generally does not have an outer coil; however, an outer coil can be provided the entire length of the guidewire if desired.

In this manner, interior space such as between the core wire and an outer coil has been substantially eliminated, and the resulting essentially solid guidewire has optimal torque transmission and resistance to rotation properties. As will be apparent to one of skill in the art, this physical characteristic is desirable along any portion of the guidewire which will carry a rotating atherectomy sleeve. Thus, in an application where the guidewire projects distally beyond the end of the rotating burr 44, conventional floppy tips can be utilized in place of the high density, low interstitial space design disclosed herein.

Although this invention is described in terms of certain preferred embodiments, other embodiments that will be apparent to those of ordinary skill in the art are also within the scope of this invention. Accordingly, the scope of the invention is intended to be defined by the claims that follow.

We claim:

1. A flexible guidewire, comprising:
   an elongate flexible core wire with a proximal segment having a first diameter and at least one distal segment having a second smaller diameter; and
   a first coil disposed about the distal segment;
   wherein the first coil is in contact with the core wire throughout the length of the coil.

2. A flexible guidewire as in claim 1, wherein the first diameter is substantially equal to the outer diameter of the coil.

3. A flexible guidewire as in claim 1, wherein the coil is securely affixed t the flexible core wire.

4. A flexible guidewire as in claim 1, wherein the first diameter is approximately 0.009 inches.

5. A flexible guidewire as in claim 1, further comprising a tapered extension of the core wire extending distally beyond the distal end of the first coil.

6. A flexible guidewire as in claim 5, further comprising a second coil surrounding said tapered extension.

7. A flexible guidewire as in claim 5, wherein the core wire has a diameter of no more than about 0.009 inches.

8. A flexible guidewire as in claim 1, wherein the first coil comprises wire having a diameter within the range of from about 0.001 inches to about 0.003 inches.

9. A rotational atherectomy catheter system, comprising:
   a source of rotational energy;
   an elongate tubular sleeve having a central lumen extending axially therethrough and rotationally linked to said source;
   a rotational cutting element on the tubular sleeve; and
   a guidewire movably disposed within said central lumen, said guidewire having a cutting element support section;
   wherein said guidewire comprises a core wire and a spring coil wrapped about and in contact with at least the cutting element support section of the core wire.

10. A method of treating an obstruction in a body lumen, comprising the steps of:
    introducing a guidewire into the body lumen, said guidewire comprising an elongate core and a coil wrapped around and in contact with at least a rotatable cutting element support section of the core, said coil extending around the core in a first rotational direction;
    advancing the guidewire to the treatment site;
    advancing a tubular sleeve over the guidewire and distally to the treatment site, said tubular sleeve having a cutting element thereon;
    positioning the cutting element over the cutting element support section of the guidewire; and
    rotating the tubular sleeve around the guidewire to treat the obstruction.

* * * * *